US008668947B2

(12) United States Patent
Groneberg-Nienstedt et al.

(10) Patent No.: US 8,668,947 B2
(45) Date of Patent: *Mar. 11, 2014

(54) METHOD OF MAKING A MOLDED FOOD ITEM FROM INDIVIDUAL FOOD PIECES

(75) Inventors: Petra Groneberg-Nienstedt, Haltern (DE); Michael Gutmann, Haltern (DE)

(73) Assignee: Nienstedt GmbH, Haltern (DE)

( * ) Notice: Subject to any disclaimer, the term of this patent is extended or adjusted under 35 U.S.C. 154(b) by 72 days.

This patent is subject to a terminal disclaimer.

(21) Appl. No.: 12/280,056

(22) PCT Filed: Feb. 20, 2007

(86) PCT No.: PCT/EP2007/051629
§ 371 (c)(1),
(2), (4) Date: May 26, 2009

(87) PCT Pub. No.: WO2007/096365
PCT Pub. Date: Aug. 30, 2007

(65) Prior Publication Data
US 2009/0280227 A1    Nov. 12, 2009

(30) Foreign Application Priority Data

Feb. 20, 2006  (DE) .......................... 10 2006 008 132
May 4, 2006   (DE) .......................... 10 2006 021 139

(51) Int. Cl.
*A23G 3/02*        (2006.01)
(52) U.S. Cl.
USPC ........... 426/512; 426/513; 426/515; 426/524; 426/389; 426/413
(58) Field of Classification Search
USPC ......... 426/513, 389, 641, 281, 413, 512, 572, 426/515, 524
See application file for complete search history.

(56) References Cited

U.S. PATENT DOCUMENTS

| | | | | |
|---|---|---|---|---|
| 2,521,995 | A | * | 9/1950 | Priddy ............................ 426/481 |
| 2,798,814 | A | * | 7/1957 | Rivoche ......................... 426/574 |
| 3,728,136 | A | | 4/1973 | Langlands |
| 4,036,997 | A | * | 7/1977 | VerBurg ......................... 426/272 |
| 4,276,314 | A | | 6/1981 | Andersen |
| 4,626,436 | A | * | 12/1986 | Bradley et al. ................ 426/289 |
| 4,868,951 | A | | 9/1989 | Akesson et al. |
| 4,973,492 | A | | 11/1990 | Gibson |
| 5,223,297 | A | | 6/1993 | Theys et al. |
| 5,518,746 | A | * | 5/1996 | Diaz ............................... 426/282 |
| 5,690,989 | A | * | 11/1997 | Clarke et al. .................. 426/641 |
| 6,826,989 | B1 | | 12/2004 | Wattles et al. |
| 2003/0044501 | A1 | | 3/2003 | Groneberg-Nienstedt et al. |
| 2003/0113422 | A1 | * | 6/2003 | Groneberg-Nienstedt et al. ............................. 426/513 |
| 2004/0231480 | A1 | | 11/2004 | Wattles et al. |
| 2005/0181099 | A1 | * | 8/2005 | Tazuke et al. .................... 426/94 |
| 2005/0282482 | A1 | | 12/2005 | Groneberg-Nienstedt |
| 2008/0038426 | A1 | | 2/2008 | Groneberg-Nienstedt et al. |
| 2009/0029027 | A1 | | 1/2009 | Groneberg-Nienstedt et al. |
| 2009/0220660 | A1 | | 9/2009 | Meunier |
| 2009/0246333 | A1 | | 10/2009 | Groneberg-Nienstedt et al. |

FOREIGN PATENT DOCUMENTS

| | | |
|---|---|---|
| DE | 22 35 517 A1 | 1/1973 |
| DE | 198 06 391 A1 | 8/1999 |
| DE | 101 41 989 A1 | 4/2003 |
| DE | 101 64 637 A1 | 6/2003 |
| DE | 102 20 006 A1 | 11/2003 |
| DE | 10 2005 016 159 A1 | 10/2006 |
| EP | 0 168 909 A2 | 1/1986 |
| EP | 0 288 592 A1 | 11/1988 |
| EP | 1 470 754 A1 | 10/2004 |
| EP | 1 156 720 B1 | 2/2005 |
| EP | 1 595 456 A2 | 11/2005 |
| FR | 2 847 427 A1 | 5/2004 |
| GB | 2 280 869 A | 2/1995 |
| WO | WO 97/10717 A1 | 3/1997 |
| WO | WO 03/077662 A1 | 9/2003 |
| WO | WO 2006/053601 A1 | 5/2006 |
| WO | WO 2006/105821 A1 | 10/2006 |
| WO | WO 2007/085773 A1 | 8/2007 |

OTHER PUBLICATIONS

Author anonymous, Abstract of "Finger foods—new process offers exciting possibilities," FTSA database-Database Accession No. 86-3-10-g0028 regarding Food Review, vol. 13, No. 1, 1986, p. 19, one page.
Office Action mailed on Feb. 22, 2012 regarding U.S. Appl. No. 12/280,064.

* cited by examiner

*Primary Examiner* — Drew Becker
*Assistant Examiner* — Preston Smith
(74) *Attorney, Agent, or Firm* — Andrew Wilford

(57) ABSTRACT

A first preliminary product comprising individual frozen pieces of a first food and a second preliminary product comprising individual frozen pieces of a second food are combined by precompacting the frozen individual pieces of the first preliminary product in a premolding process so as to form a concavity in the first preliminary product and placing the frozen individual pieces of the second preliminary product into the concavity of the first preliminary product to form a single frozen starting product that is put into at least one mold cavity. There the single frozen starting product is molded into a ready-to-prepare frozen end product by compacting the single frozen starting product.

36 Claims, No Drawings

METHOD OF MAKING A MOLDED FOOD ITEM FROM INDIVIDUAL FOOD PIECES

Applicants claim, under 35 U.S.C. §119, the benefit of priority of 1) the filing date of Feb. 20, 2006 of a German patent application, copy attached, Serial Number 10 2006 008 132.3, filed on the aforementioned date, and 2) the filing date of May 4, 2006 of a German patent application, copy attached, Serial Number 10 2006 021 139.1, filed on the aforementioned date, the entire contents of each of which are incorporated herein by reference.

BACKGROUND OF THE INVENTION

1. Field of the Invention

The present invention relates to a method for producing ready-to-prepare molded food items from individual pieces of vegetables, including rice or potatoes, fruit, meat, poultry, game, fish or seafood, pasta, pastry or a combination of some or all of these ingredients.

2. Description of the Related Art

It is known from fish, meat or poultry processing to process frozen pieces of the foodstuff in order to form a molded end product. Such a method is described for example in WO 97/10717. In said document, pieces of meat which are already in the subsequently desired shape are formed from a slab-type material under the effect of pressure.

It is known from EP 0 168 909 to produce a frozen block of vegetables or fruits via a shaping method. In this method, frozen products are processed in order to produce therefrom firstly blocks and subsequently individual portions of a foodstuff. The main use of this method is for example to produce portioned pieces of spinach, which can then be removed from the packaging on a portion-by-portion basis. After thawing these portion pieces, the product is then prepared in the conventional manner, wherein the bonding that took place during the freezing operation is dissolved as a result of the preparation process and the product breaks down into a ready-to-eat food item.

The disadvantage of this method is that the use is restricted to foodstuffs which break down into individual parts as a result of the preparation process after thawing of the intermediate product.

In addition to this method, other methods are known for producing potato products from mashed potatoes. For instance, U.S. Pat. No. 4,276,314 discloses a method for producing so-called hash-brown potatoes, in which mashed potato products are brought into the desired product shape prior to deep-freezing and then are frozen. After being thawed again, these products are then fried and prepared to make them ready to eat. This method is not suitable for producing products which are molded only by the actual shaping process, but rather the method requires an additional external bond or a frying process which is able to quickly produce an outer shell of suitable strength in order thus to avoid disintegration of the product. The entire contents of U.S. Pat. No. 4,267,314 are incorporated herein by reference.

SUMMARY AND OBJECTS OF THE INVENTION

An object of the present invention is thus to provide a method for producing ready-to-prepare or even ready-to-eat food items, by which not only meat but also vegetables can be molded to form a cookable end product such that the meat, the vegetables or the combination thereof can be cooked in the frozen state without disintegrating or losing the essential shape, wherein a prior treatment of the end product, for example by coating with breadcrumbs or marinating, is not ruled out.

According to the present invention, this object is achieved in that the method includes the steps: combining the ingredients to form starting products including frozen individual pieces, introducing the starting products continuously or in batches into at least one mould cavity and molding the frozen starting products to form a ready-to-bake or ready-to-cook frozen end product by compacting the starting products located in the mold cavity so as to mold the ready-to-prepare food items.

One important novel feature of the present invention is the fact that the frozen starting products can be processed to form a ready-to-bake or ready-to-cook frozen end product by being compressed in the frozen state in the mold cavity to form the desired shape. The products thus produced can then be cooked during a preparation process, for example in an oven or else in a frying pan, even without further treatment and while retaining the shape. It is also possible for the products to be produced in such a way that they are deliberately intended to disintegrate during the further preparation in order to give the impression of being prepared from foodstuffs processed in the natural or similar form.

One preferred use of the method according to the present invention lies in the production of products including frozen chips or sections thereof. To this end, relatively small pieces of potato are used as starting products and are placed in the deep-frozen state in a mold cavity which corresponds to the shape of a chip-like potato stick. The deep-frozen sections are then compacted, so that a deep-frozen potato stick is obtained as a ready-to-prepare food item. This can then be processed in the conventional manner in an oven or in a deep-fat fryer. As a result, it is possible to process even products that are too small or too short, in order to produce approximately genuine chips from these previously unused leftover products.

The method according to the present invention can be used to produce all types of food items from frozen individual pieces. The individual pieces used may be vegetables, fruit, meat, poultry, game or fish or other seafood. The individual pieces may also be a combination of some or all of these ingredients. In a first step, the required individual pieces are combined, which in particular entails sorting by size and weight.

DESCRIPTION OF THE PREFERRED EMBODIMENT(S) OF THE INVENTION

The starting products of course need only be large enough for the desired end products to be produced therefrom. Although in principle the use of the present invention in conjunction with mashed or ground products is possible, nevertheless one important field of use of the present invention includes using starting products which are smaller than the subsequent end products but which are still whole pieces of the original material. The starting products selected and frozen in this way are then molded by being compacted in the mould cavity to form the end product, with the ingredients remaining frozen during the entire processing operation.

In the case of some products, it has been found that only by compacting the starting products at low temperatures do the products remain so firmly bonded to one another that disintegration during the subsequent preparation process, which of course entails thawing of the end products, can be avoided.

However, the bonding of the individual pieces can be improved prior to freezing of the individual pieces or else prior to compaction and even thereafter by adding additional adhesion promoters. In the simplest case, this may be a liquid, in particular water or a protein-containing liquid, which improves the bonding of the individual pieces.

Before combining the starting products to form the frozen individual pieces, the products that are too large and also the products that are too small are removed. Products that are too large may either be fed to some other processing operation or else they may be subjected to a process for making them smaller so that they can again be fed to the actual method. Products that are too small are further processed in some other way in a conventional manner.

The adhesion force between the individual pieces can furthermore be increased if the individual pieces are thawed before being introduced into the mould cavities. As a result, during subsequent deep-freezing prior to the actual compaction operation, it is already possible to produce tacky bonds by freezing the individual parts to one another. It is also possible to spray the frozen or thawed starting products with additional water or other liquids.

Another particularly advantageous embodiment of the method according to the present invention makes it possible to produce an assembly of several preliminary products to form a ready-to-eat end product. For example, a preliminary product of a first type can be produced from a mixture of individual pieces and either already pre-compacted in a premolding process so that then, in a second step, a mixture of a second preliminary product produced in the same way can be compacted together with this first preliminary product or combined therewith in some other way. For instance, a bowl-shaped item made of rice may be produced as the first preliminary product while a sauce/vegetable mixture or a meat filling is used as the second preliminary product.

The first preliminary product may then have a concave shape, while the second preliminary product is placed in the bowl-like recess of the concave first preliminary product. Depending on the user's requirements, the first preliminary product may also be configured such that it disintegrates during the cooking process, so that the second preliminary product of stable shape then comes to lie in a bed of the disintegrated first preliminary product. In one example, the first preliminary product may for instance be the aforementioned rice edging, while the second preliminary product is then for example a mixture of vegetables and fruit. A meat product can also be arranged within a rice edging in this way.

Before being compacted in the mold cavity, the individual pieces may be provided with further additives. This may be for example a marinade or else a powder-type seasoning. In order to be able more easily to remove from the mold cavities the end products produced after compacting, it is possible to heat the mould cavities slightly so that the outer layer of the end product melts and thus prevents it from being frozen solid to the wall of the mould cavity.

In principle, the present invention is characterised in that preferably mainly or entirely vegetable or fruit pieces are processed using the method. These pieces are deep-frozen, sorted according to size and then compacted in the deep-frozen state either without or with the addition of further adhesion promoters or further flavor enhancers to form a ready-to-prepare end product of stable shape, whereby shape stability means that the food item produced in this way does not fall apart during the further processing, in particular during the thawing brought about by the heat of the preparation process.

The invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing description.

We claim:

1. A method for producing molded ready-to-prepare food items, the method comprising the steps of:
   combining a first preliminary product comprising individual frozen pieces of a first food and a second preliminary product comprising individual frozen pieces of a second food to form a single frozen starting product by:
   precompacting the frozen individual pieces of said first preliminary product in a premolding process so as to form a concavity in said first preliminary product; and
   placing the frozen individual pieces of said second preliminary product into a concave section of said first preliminary product precompacted to the concavity to form said single frozen starting product;
   introducing said single frozen starting product continuously or in batches into at least one mold cavity; and
   molding said single frozen starting product to form a ready-to-prepare frozen end product by compacting said single frozen starting product located in said at least one mold cavity so as to mold said ready-to-prepare food items.

2. The method according to claim 1, further comprising the step of:
   adding a liquid to said frozen individual pieces before introduction into said at least one mold cavity in order to improve bonding of said frozen individual pieces.

3. The method according to claim 2, wherein said liquid is selected from the group consisting of water and a protein-containing liquid.

4. The method according to claim 1, further comprising the step of:
   rendering tacky the individual frozen pieces of said first food by sprinkling with a liquid.

5. The method according to claim 4, further comprising the step of:
   rendering tacky the individual frozen pieces of said second food by sprinkling with said liquid.

6. The method according to claim 1, further comprising the step of:
   seasoning said frozen individual pieces before compacting in said at least one mold cavity.

7. The method according to claim 6, wherein said seasoning is carried out by adding a marinade or a powder-type seasoning.

8. The method according to claim 1, further comprising the step of:
   demolding the compacted frozen starting product from said at least one mold cavity.

9. The method according to claim 8, further comprising the step of:
   heating walls of said at least one molding cavity prior to said demolding operation in order to allow easier demolding of said compacted frozen starting products.

10. The method according to claim 1, wherein, further comprising the step of:
    rendering tacky the individual frozen pieces of said second food by sprinkling with a liquid.

11. The method according to claim 1, further comprising the step of:
    preshaping said first preliminary product to include a bowl-like recess as said concave section as said second preliminary product is placed in said bowl-like recess.

12. The method according to claim 1, further comprising the step of:

feeding said ready-to-prepare frozen end product to a cooking process.

13. The method according to claim 12, wherein said cooking process disintegrates said first preliminary product so that said second preliminary product lies in a bed of said disintegrated first preliminary product.

14. The method according to claim 12, wherein the cooking process is effected in an oven or in a deep-fat fryer.

15. The method according to claim 14, wherein said cooking process disintegrates said first preliminary product so that said second preliminary product lies in a bed of said disintegrated first preliminary product.

16. The method of claim 1, wherein said first food is rice and said second food is a meat filling, a meat product, a sauce/vegetable mixture, or a mixture of vegetables and fruit.

17. The method of claim 16, wherein said second food is said sauce/vegetable mixture.

18. The method of claim 16, wherein said second food is said meat filling.

19. The method according to claim 16, further comprising the step of:
adding a liquid to said frozen individual pieces before introduction into said at least one mold cavity in order to improve bonding of said frozen individual pieces.

20. The method according to claim 19, wherein said liquid is water or a protein-containing liquid.

21. The method according to claim 16, further comprising the steps of:
thawing said frozen individual pieces before introduction into the one mold cavity; and
freezing said thawed individual pieces after molding in the one mold cavity.

22. The method according to claim 16, further comprising the step of:
rendering tacky the frozen individual pieces of said first food by sprinkling with a liquid.

23. The method according to claim 22, further comprising the step of:
rendering tacky the frozen individual pieces of said second food by sprinkling with said liquid.

24. The method according to claim 16, further comprising the step of:
seasoning said frozen individual pieces before compacting in said at least one mold cavity.

25. The method according to claim 24, wherein said seasoning is carried out by adding a marinade or a powder-type seasoning.

26. The method according to claim 16, further comprising the step of:
demolding said compacted frozen starting products from said at least one mold cavity.

27. The method according to claim 26, further comprising the step of:
heating walls of said at least one molding cavity prior to demolding in order to allow easier demolding of said compacted frozen starting products.

28. The method according to claim 16, further comprising the step of:
rendering tacky the frozen individual pieces of said second food by sprinkling with a liquid.

29. The method according to claim 16, wherein said first preliminary product is preshaped to include a bowl-like recess as said concave section as said second preliminary product is placed in said bowl-like recess.

30. The method according to claim 16, further comprising the step of:
feeding said ready-to-prepare frozen end product to a cooking process.

31. The method according to claim 30, wherein said cooking process disintegrates said first preliminary product so that said second preliminary product, which has a stable shape, lies in a bed of said disintegrated first preliminary product.

32. The method according to claim 30, wherein the cooking process is carried out in an oven or a deep-fat fryer.

33. The method according to claim 32, wherein said cooking process disintegrates said first preliminary product so that said second preliminary product lies in a bed of said disintegrated first preliminary product.

34. A method for producing molded ready-to-prepare food items, the method comprising the steps of:
combining frozen individual pieces of a first preliminary product of a first food and frozen individual pieces of a second preliminary product of a second food to form a single frozen starting product by:
precompacting the frozen individual pieces of said first preliminary product in a premolding process so as to form a concavity in said first preliminary product; and
placing the frozen individual pieces of said second preliminary product into a concave section of said first preliminary product precompacted into the concavity to form said single frozen starting product;
thawing said frozen individual pieces so as to produce a thawed single starting product; and
introducing said thawed single starting product continuously or in batches into at least one mold cavity; and
molding said single frozen starting product to form a ready-to-prepare end product by compacting said thawed single starting product located in said at least one mold cavity so as to mold said ready-to-prepare food items; and
freezing the ready-to-prepare end product after said molding so as to generate a final single frozen starting product.

35. The method of claim 34, wherein said first food is rice and said second food is a meat filling, a meat product, a sauce/vegetable mixture, or a mixture of vegetables and fruit.

36. The method of claim 35, wherein said second food is said sauce/vegetable mixture.

* * * * *